US00PP12367P2

(12) United States Plant Patent
Utecht

(10) Patent No.: US PP12,367 P2
(45) Date of Patent: Jan. 22, 2002

(54) GERANIUM PLANT NAMED 'FISBAROCK'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/631,663

(22) Filed: Aug. 3, 2000

(51) Int. Cl.[7] ..... A01H 5/00
(52) U.S. Cl. ..... Plt./332
(58) Field of Search ..... Plt./332, 324

(56) References Cited

PUBLICATIONS

2001 Fischer–Schmülling Plant Alliance Catalog featuring 'Fisbarock' on p. 27.
Swiss Application for 'Fisbarock'.
European Union Application for 'Fisbarock'.
German Application for 'Fisbarock'.
German Grant for 'Fisbarock'.
Canadian Application, proposed denomination, Plant Varieties Journal, No. 33; Oct. 1999 (Canada).
GTITM UPOVROM Citation for 'Fisbarock' as per QZ PBR 980829; Jun. 15, 1998.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisbarock', as described and illustrated, and particularly characterized by the combined features of dark-red, double flowers, medium-green, only slightly zoned foliage, medium flowering response, and relatively vigorous, though dense and well-branched, growth habit.

2 Drawing Sheets

BACKGROUND OF THE INVENTION

The present invention relates to a new and distinct cultivar of geranium plant, botanically known as *Pelargonium peltatum,* and hereinafter referred to by the cultivar name 'Fisbarock'.

'Fisbarock' is a product of a planned breeding program which had the objective of creating new ivy geranium cultivars with dark-red, double flowers in combination with moderately vigorous growth and well-branched plant habit.

'Fisbarock' originated from a hybridization made by the inventor, Angelika Utecht, in a controlled breeding program in Galdar, Gran Canaria, Spain, in 1994. The female parent was the variety 'Fisbliz' (U.S. Plant Pat. No. 9,373), characterized by white, single-type flowers, medium-green foliage with slight zonation and vigorous growth. The male parent was a hybrid seedling, designated no 323-1 (unpatented), derived from a cross between the commercial variety 'Guishiva' (U.S. Plant Pat. No. 9,351) and the variety 'Fisam' (U.S. Plant Pat. No. 8,327). 'Guishiva' is characterized by deep-red, semi-double flowers, small leaves with distinct zonation and relatively compact growth habit. 'Fisam' is characterized by light-violet, double flowers, zoned foliage and comparatively vigorous growth.

'Fisbarock' was selected as one flowering plant within the progeny of the stated cross by the inventor, Angelika Utecht, in 1995 in a controlled environment in Galdar, Gran Canaria, Spain.

The first act of asexual reproduction of 'Fisbarock' was accomplished when vegetative cuttings were taken from the initial selection in autumn 1995 in a controlled environment in Galdar, Gran Canaria, Spain, by, or under the supervision of, Angelika Utecht. Horticultural examination of plants grown from these cuttings, initiated in the spring of 1996 in Hillscheid, Germany, and continuing thereafter, has demonstrated that the combination of characteristics as herein disclosed for 'Fisbarock' are firmly fixed and are retained through successive generations of asexual reproduction.

BRIEF DESCRIPTION OF THE INVENTION

The following traits have been repeatedly observed and are determined to be basic characteristics of 'Fisbarock', which in combination distinguish this geranium as a new and distinct cultivar:

1. Dark-red, double flowers;

2. Relatively large, semi-spherically-shaped inflorescences;

3. Medium-green, relatively large, slightly zoned foliage;

4. Moderately vigorous growth and medium-tall, well-branched plant habit; and

5. Medium spring flowering response.

'Fisbarock' has not been observed under all possible environmental conditions. The phenotype of the new cultivar may vary significantly with variations in environment such as temperature, light intensity and day length without any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fisbarock' is the variety 'Fisrock' (U.S. Plant Pat. No. 10,365). In comparison to 'Fisrock', 'Fisbarock' has an almost similar flower color, somewhat larger flowers and inflorescences, wider, only slightly zoned leaves, and a different plant habit. 'Fisbarock' grows generally more vigorously and develops up to twice the number of branches as 'Fisrock', thus forming a dense, bushy and moderately-tall plant. 'Fisrock' has a more upward developing plant habit and 'Fisbarock' is rather flat-spreading or trailing.

BRIEF DESCRIPTION OF THE DRAWINGS

The accompanying photographic illustrations show typical flower and foliage characteristics of 'Fisbarock' with colors being as true as possible with illustrations of this type.

Sheet 1 is a side view of a 'Fisbarock' plant in a hanging basket.

Sheet 2 is a close-up view of the inflorescence, buds and leaves.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium peltatum L'Hérit ex Aiton.*

*Commercial.*—Ivy geranium, cv. 'Fisbarock'.

Inflorescence:

*Type.*—Umbel. Shape: Almost semi-spherical. Average diameter: 95 mm. Average depth: 50 mm. Peduncle length: 130 mm. Peduncle color: Green, RHS 143 A, no anthocyanin. Pedicel length: 31 mm, with spur. Pedicel color: Green, about RHS 137 C. Number of flowers per umbel: About 8–10. Lastingness of the umbel: Approximately 13 days at 18° C.

*Corolla.*—Average diameter: 55 mm. Form: double. Shape: Relatively large, nearly round. Number of petals: 16.9. Size: Upper petals are 33–34 mm long, 22–25 mm wide; lower petals are approximately 25–27 mm long and 17–18 mm wide. Shape: Spatulate narrow, obovate; attenuate base; upper end is truncate or rounded; margin entire, only at apex slight dentation may occure. Color (gneral tonality from a distance of three meters): Dark-red. Color of upper petals: Coloration between RHS 46 A–RHS 46 B. Markings of upper petals: Two blackish veins, RHS 187 A, surrounding a violet stripe, RHS 74 B. Color of lower petals: Coloration between RHS 46 A–RHS 46 B. Color of lower surface of petals: Near RHS 57 A with strong black veins, RHS 187 A. Number of petaloids: 1–2. Color of petaloids: Upper surface color approximately RHS 46 B, lower surface color approximately RHS 53 C. Color of sepals: Outer surface is light green, RHS 143 B; inner surface is light green, RHS 143 C; no anthocyanin. Number of sepals: 5. Size of sepals: 13–14 mm long; 5 mm wide for the largest upper sepal; 2–3 mm in width for the other sepals. Shape of sepals: Linear to lanceolate; acute tip; truncate base; surface with moderate pubescence; margin entire.

*Bud (just before petals unfold).*—Shape: Elliptical. Color (sepals): Light-green, RHS 137 D. Color (petals): Uniformly dark-red, RHS 46 A. Length: 17 mm. Width: 10 mm.

*Reproductive organs.*—Androecium: 7 fertile anthers, with whitish filaments that are pink near the top end and with orange pollen, RHS 33 A; pollen amount produced is plenty. Gynoecium: 5–6-lobed, dark-red stigma and white to pink filament, 1 pistil per flower. Fertility/seed set: No spontaneous seed set observed.

*Spring flowering response period.*—In Hillscheid, Germany, in 1999, plants had on average 0.6 flowers opened 12 weeks after planting of rooted cuttings (pinched plants).

*Outdoor flower production.*—Medium to rich flowering, the flower count in 1999, in Hillscheid, Germany, indicated about 3.75 inflorescences per plant in mid-May.

*Durability.*—Good shatter resistance and relatively good rain resistance for a double-form flower; the petal color may fade to approximately RHS 53 C or RHS 53 D, when maturing.

*Lastingness of the individual bloom.*—Approximately 7–8 days at 18° C.

*Fragrance.*—None.

Plant:

*Foliage.*—Shape: Ivy-shaped with weak, rounded and slightly overlapping lobes, base cordate, rounded tips, margin entire. Texture: Upper surface smooth and slightly glossy. Margin: Entire, apart from the lobes. Size of leaf: 92 mm wide, 46 mm long. Color of upper surface: Medium-green, approximately between RHS 137 B–RHS 137 C. Color of lower surface: Near RHS 137 D. Color of zonation: Weak on young leaves, RHS 174 A; may not be visible on mature leaves during the summer. Petioles: 65–75 mm long, 2–3 mm diameter; light green in color, approximately RHS 144 B.

*General appearance and form.*—Internode length: 20–30 mm. Branching pattern: 15.7 branches. Size of plant/Length of branches: 21.5 cm (12 weeks after planting) as measured from the top of the soil (base of main stem) to the tips of the branches, 60–65 cm (in early September, 30 weeks from planting).

Disease/pest resistance/susceptibility: None observed to date.

I claim:

1. A new and distinct cultivar of geranium plant named 'Fisbarock', as described and illustrated.

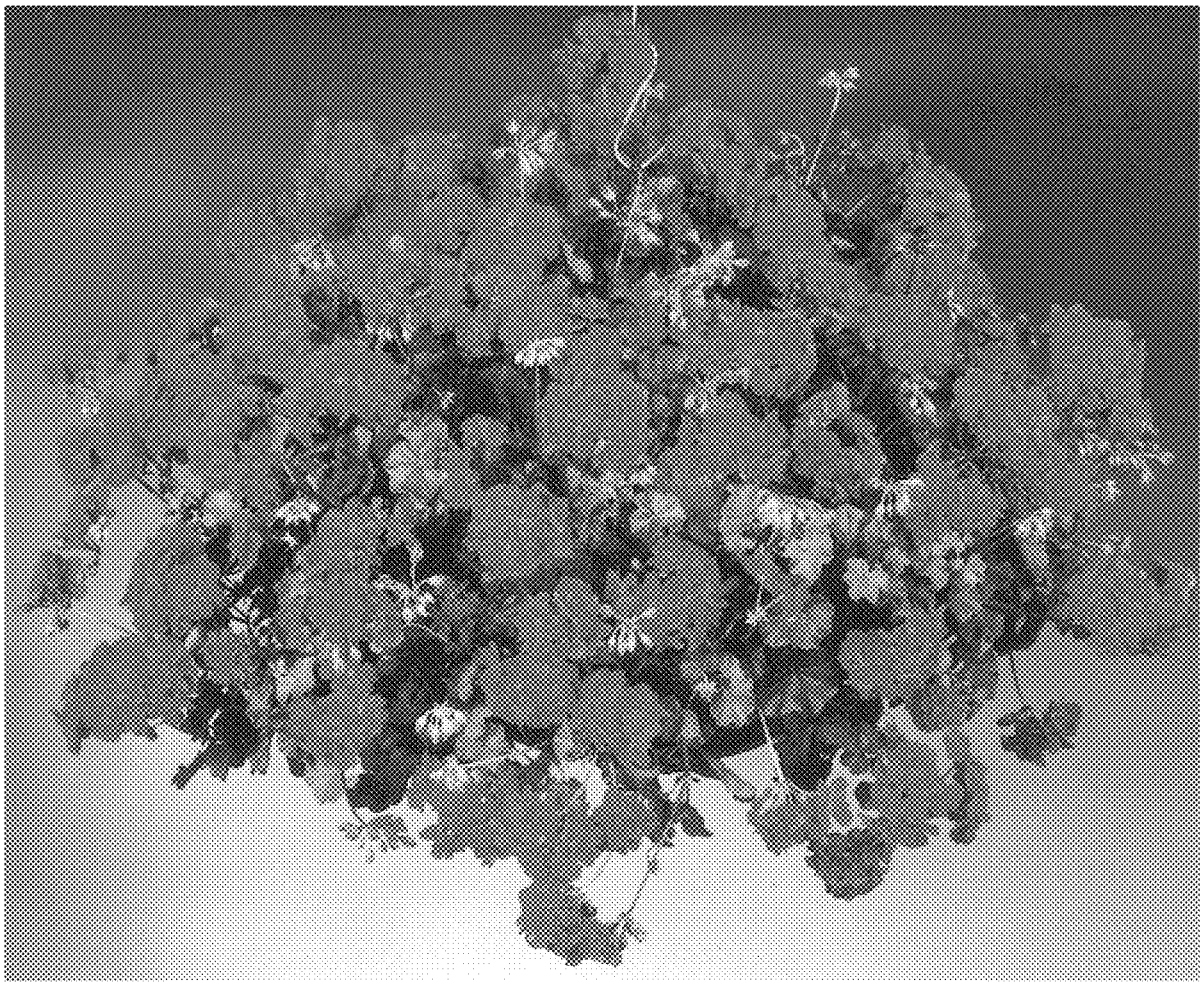

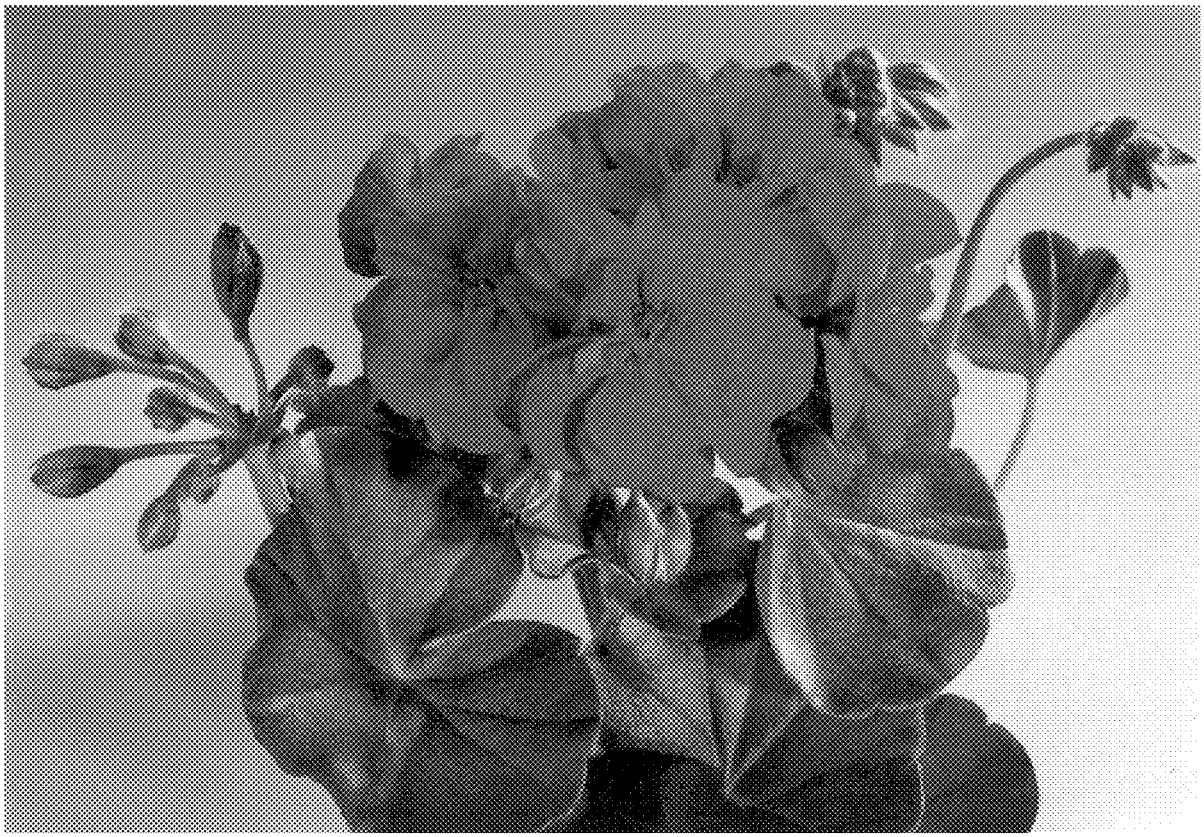

* * * * *